United States Patent [19]

Kendall et al.

[11] Patent Number: 5,269,314
[45] Date of Patent: Dec. 14, 1993

[54] STETHOSCOPE COVER

[76] Inventors: Dwain Kendall, 203 Meredith St., High Point, N.C. 27260; Saundra K. Morris, 27 Apple Seed La., Gaithersburg, Md. 20878

[21] Appl. No.: 818,346
[22] Filed: Jan. 9, 1992
[51] Int. Cl.⁵ ............................................. A61B 5/02
[52] U.S. Cl. ................................... 128/715; 181/131
[58] Field of Search ................ 181/126, 131, 137; 128/715, 773, 67; 4/242

[56] References Cited

U.S. PATENT DOCUMENTS

| | | | |
|---|---|---|---|
| 1,344,655 | 5/1920 | Rubin | 181/137 |
| 1,410,034 | 3/1922 | Pollard | 181/137 |
| 1,425,158 | 8/1922 | Wolfshon | 128/67 |
| 2,035,384 | 3/1936 | Hinchliff | 215/100.5 |
| 2,651,380 | 9/1953 | Brandenburg | 181/137 |
| 2,910,705 | 11/1959 | Coplan | 4/242 |
| 4,461,368 | 7/1984 | Plourde | 181/137 X |
| 4,589,149 | 5/1986 | Bassi | 4/242 |
| 4,867,268 | 9/1989 | Ulert | 181/137 |
| 4,871,046 | 10/1989 | Turner | 181/131 |
| 4,995,473 | 2/1991 | Packard | 181/131 |

OTHER PUBLICATIONS

The George P. Pilling & Son, Philadelphia 1932-1933.

*Primary Examiner*—Lee S. Cohen
*Assistant Examiner*—Samuel Gilbert

[57] ABSTRACT

A patient's discomfort from a cold stethoscope head is avoided by a disposable fabric cover. The cover is disposed between the stethoscope face and the patient's skin and permits the patient's chest sounds and the like to be transmitted through to the stethoscope face at a sufficient level to be amplified and rendered audible by the stethoscope. Such sound transmission may be through the fabric itself or through a port defined in the fabric radially inward from the periphery of the stethoscope face. An elasticized outer hem permits the cover to be easily placed onto and removed from the stethoscope. The inexpensive cover can be economically discarded after a single use and replaced so as to avoid transmission of contagious diseases between successive patients examined with the same stethoscope.

9 Claims, 1 Drawing Sheet

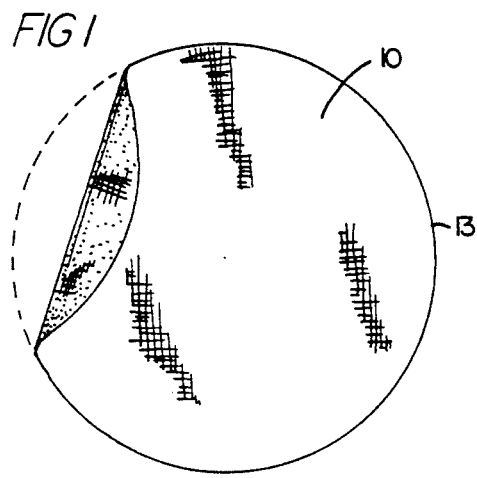
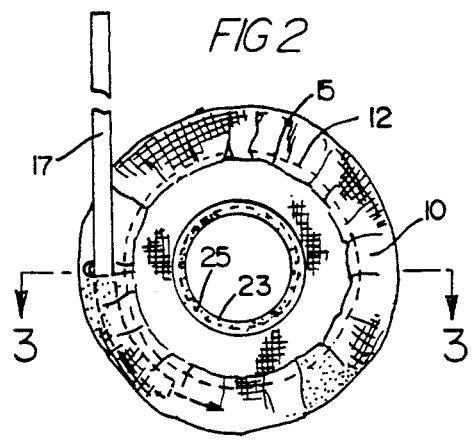
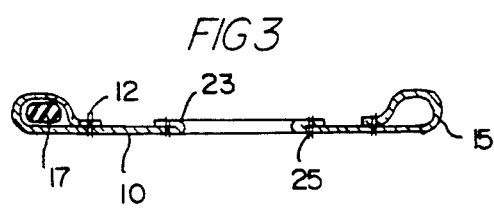
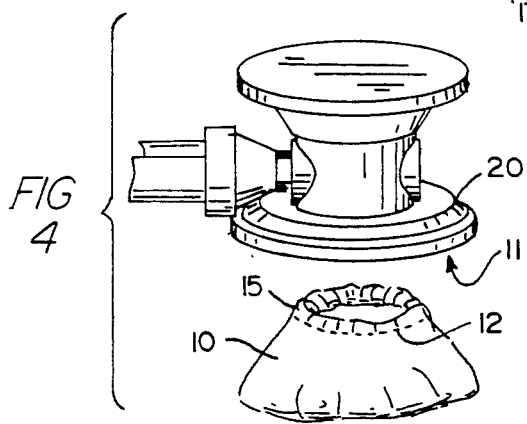
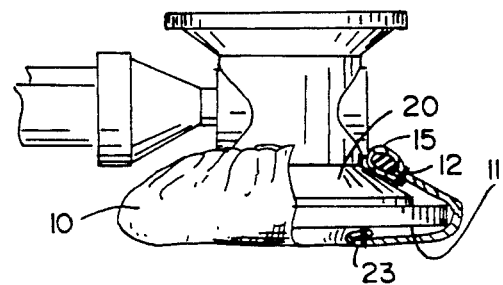
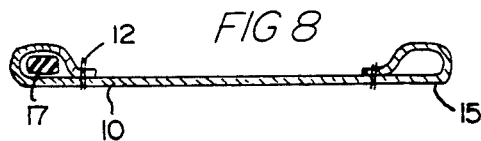
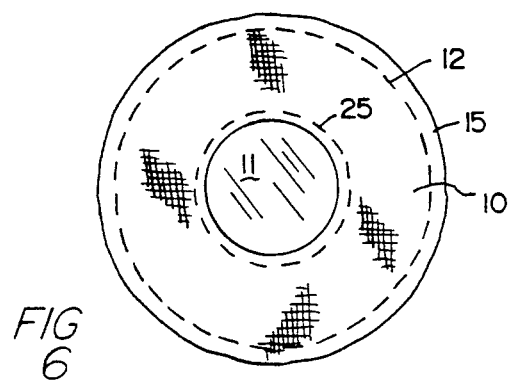
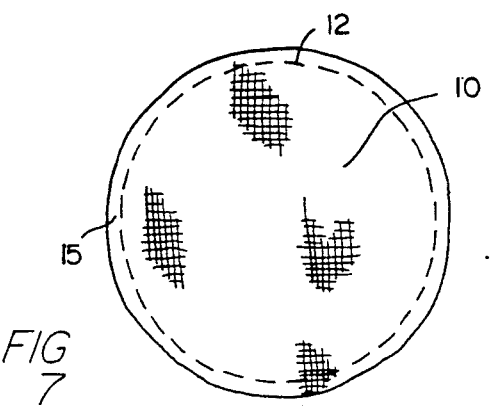

STETHOSCOPE COVER

BACKGROUND OF THE INVENTION

1. Technical Field

The present invention relates to a method and apparatus for preventing discomfort to a patient being examined with a stethoscope. The method and apparatus also prevents transmission of contagious diseases between patients successively examined with the same stethoscope.

2. Discussion of the Prior Art

An almost universally shared experience is the discomfort felt by a patient when a physician places the relatively cold face of a stethoscope head against the patient's body. The prior art has addressed this problem in two primarily different ways. In one approach the stethoscope head is stored in an insulated or heated holder prior to use in order to prevent the head from cooling down significantly below the human body temperature. This approach requires the physician to wear objectionable equipment such as the holder and, if the holder is heated, a battery pack. Moreover, there is considerable inconvenience in having to remove the stethoscope from the holder before use and to replace it in the holder after use.

In a second prior art technique the stethoscope head is maintained at a constant comfortable temperature by an electrical heater built into the stethoscope. While somewhat more convenient to use than the separately supported stethoscope, the built in heater adds considerable expense to the unit. In addition, it has been found that when the heater batteries wear out, physicians tend to forget or otherwise neglect to replace them. As a consequence, after some limited time period the stethoscope, in spite of its built-in heater, is no longer thermally comfortable for patients.

A totally separate problem associated with stethoscopes relates to examination of a patient having a contagious disease. Under such circumstances it is not clinically desirable for the stethoscope to be reused for another patient without first sterilizing the stethoscope. Sterilizing the stethoscope, on the other hand, is inconvenient, time consuming and expensive.

OBJECTS AND SUMMARY OF THE INVENTION

It is an object of the present invention to provide a method and apparatus for preventing thermal discomfort to a patient being examined with a stethoscope.

It is another object of the present invention to provide an inexpensive and easy to use article of manufacture for thermally insulating a stethoscope without impairing the primary function of the stethoscope, namely monitoring sounds from portions of the human body placed in contact with the face of the stethoscope head.

A further object of the invention is to provide a method and apparatus for protecting a patient against both thermal discomfort and transmission of contagious diseases when being examined with a stethoscope.

In accordance with the present invention a disposable fabric cover for a stethoscope head is interposed between the stethoscope face and the patient's skin to provide thermal insulation while permitting acoustic transmission of chest sounds and the like. If the fabric is transmissive of sound, the cover overlies the entire front face of the stethoscope head. If the fabric significantly attenuates sound, a hole is provided in the cover so that only the periphery of the stethoscope face is covered. In either case, a circular piece of material is provided with an elastic periphery sized to be expanded over the stethoscope head and close over the rear side of the head. If acoustically non-transmissive material is used, an opening is substantially centered over the stethoscope face. The portion of the cover material overlying the front surface is interposed between the stethoscope face and the patient's body when the stethoscope is in use, thereby preventing the stethoscope face from directly contacting the patient's skin. The patient is thus protected from the discomfort of the cold stethoscope head. The inexpensive fabric permits disposability of the cover after a single use, thereby protecting the patient from contracting contagious diseases through multi-patient use of the stethoscope.

BRIEF DESCRIPTION OF THE DRAWINGS

The above and still further objects, features and advantages of the present invention will become apparent upon consideration of the following detailed description of a specific embodiment thereof, particularly when taken in conjunction with the accompanying drawings wherein like reference numerals from the various figures are utilized to designate like components, and wherein:

FIG. 1 is a plan view of a piece of fabric used as the starting material for forming the stethoscope cover of the present invention;

FIG. 2 is a rear view in plan of the stethoscope cover of the present invention during fabrication;

FIG. 3 is a view in section taken along lines 3—3 of FIG. 2;

FIG. 4 is an exploded view of a stethoscope and the stethoscope cover of the present invention prior to placement of the cover on the stethoscope head;

FIG. 5 is a side view in elevation of a stethoscope head showing the stethoscope cover disposed over one face thereof;

FIG. 6 is a front view in elevation of the stethoscope head and stethoscope cover illustrated in FIG. 5;

FIG. 7 is a front view in elevation of the stethoscope head and modified stethoscope cover according to another embodiment of the invention; and FIG. 8 is a view in section similar to FIG. 3 but of the modified cover of FIG. 8.

DESCRIPTION OF THE PREFERRED EMBODIMENT

Referring to the drawings in greater detail, the stethoscope cover of the present invention is formed from a generally circular piece of fabric 10 (FIG. 1). The fabric may be any natural or synthetic woven, non-woven, knitted, blown fiber or other fabric sheet having a thickness sufficient to prevent a relatively cool stethoscope head from causing thermal discomfort to the skin of a patient when the sheet is interposed between the stethoscope head and the patient's skin. Examples of suitable natural fabrics are flannels of cotton or wool or blends thereof, and the preferred natural fabric is outing flannel, a light cotton flannel with a short nap. Examples of suitable synthetic fabrics are: rayon; nylon; fabric materials prepared from polyesters, such as polyethylene terephthalate; acrylics, such as acrylonitrile; vinyl polymers, such as vinyl chloride, vinylidene chloride, vinyl acetate, ethylene, propylene, vinylidene flouride, tetraflouroethylene, as well as copolymers and interpolymers thereof. Laminates of two or more synthetic fabrics or combinations of synthetic and natural fabrics may also be employed. In general, any fabric material capable of serving the functions described herein may be employed. The diameter of piece 10 is chosen to be larger than the diameter of the front face 11 of the stethoscope head 20 with which the cover is to be employed. In an exemplary embodiment of the invention the diameter of cloth piece 10 is typically on the order of three inches.

The outer edge 13 of starting piece 10 is turned in and stitched to the main body of piece 10 at 12 to form an outer annular hem 15 about the entire piece periphery. In the exemplary embodiment the radial dimension of hem 15 is approximately one-half inch. As best illustrated in FIGS. 2 and 3, a small cut is made in hem 15, or stitching 12 is provided with a suitable gap, in order to permit an elastic strip 17 to be inserted into the hem. The ends of elastic strip are joined together by tying or sewing to form an endless strip inside the hem having a length, when relaxed or unstretched, that is less than the circumference of the front face 11 of stethoscope head 20. In the exemplary embodiment the elastic strip 17 has a width on the order of one-eighth inch. The opening through which the strip is inserted may be sewn closed after the elastic strip 17 is pulled entirely through the hem. Alternatively, the hem 15 may be formed about the elastic strip, the ends of which are extended out through a suitably provided opening. After the hem is stitched the ends of the elastic strip may be pulled through the opening to contract the hem to the desired annular size, and the ends of the strip are then joined together and the excess ends thereof cut off and discarded.

If the fabric employed for starting piece 10 is not transmissive of chest sounds at a level suitable for amplification by a stethoscope, the cover must be provided with an aperture or port to transmit such sounds. Under such circumstances a central opening, preferably circular, is cut in the center of piece 10 and its edge is folded radially outward to form an inner annular hem 23. Stitching 25 secures inner hem 23 in place. The diameter of the resulting central port is less than the diameter of the stethoscope face 11 and, in the exemplary embodiment, is one and one-half inches; the radial dimension of hem 23 is approximately one-quarter inch. The inner hem may be provided with an elastic strip inserted into the hem in the same manner described above for strip 17 in the outer hem.

The stethoscope cover of the present invention is utilized by placing it over the stethoscope head 20 in a manner such that a portion of face 11 is exposed through the central port surrounded by inner hem 23. This deployment is effected by stretching the elasticized outer hem 15 and passing it over the periphery of stethoscope face 11. With outer hem 15 disposed rearward of face 11, the hem may be released to permit it to contract against the rear surface of the stethoscope head. When thusly positioned the cover is oriented with its central opening or port (if such is provided) substantially centered on stethoscope face 11, thereby exposing the face in recessed relation to the cloth cover and permitting unimpeded transmission of chest sounds to the acoustic mechanism in head 20. Importantly, the fabric of the cloth cover is disposed forwardly of the stethoscope face. If the material of the cover is transmissive to chest sounds, no central port is provided and the entire front face of the stethoscope is covered (FIGS. 7 and 8). In either case, when the stethoscope is used to examine a patient, the fabric of piece 10, not the stethoscope itself, directly contacts the patient. The material of piece 10 is, for all purposes of this invention, thermally non-transmissive, thereby preventing thermal discomfort to the patient as would be caused if a cool stethoscope directly contacts the patient's skin.

The stethoscope cover of the invention also serves to prevent contamination of the stethoscope head. Specifically, the stethoscope cover is sufficiently inexpensive to be economically disposable after a single use. Therefore, after examining a patient, a physician can merely remove the cover and replace it with another, discarding the original cover. This feature is advantageous for examination of patients having contagious diseases.

The important characteristics and features of the present invention are: (1) the cover material must provide sufficient thermal insulation to prevent the relatively cold stethoscope face from causing thermal discomfort to a patient when the material is interposed between the stethoscope face and the patient's skin; (2) the cover material must be either (a) sufficiently transmissive to chest sounds to permit suitable amplification thereof by the stethoscope, or (b) provided with a sound transmission port; and (3) the cover periphery must either be elasticized or provided with other means for securing the periphery to the stethoscope head behind the front face.

From the foregoing description it will be appreciated that the invention makes available a novel stethoscope cover serving a dual function of thermally insulating the patient's skin from a cold stethoscope head while permitting economically feasible disposal of the stethoscope cover after a single use to thereby prevent transmission of contagious diseases from patient to patient.

Having described a preferred embodiment of a new and improved stethoscope cover in accordance with the present invention, it is believed that other modifications, variations and changes will be suggested to persons skilled in the art in view of the teachings set forth herein. It is therefore to be understood that all such variations, modifications and changes are believed to fall within the scope of the present invention as defined by the appended claims.

What is claimed is:

1. A method for preventing thermal discomfort to a patient being examined by a stethoscope while permitting sounds from the patient's body to be transmitted to the stethoscope head, said method comprising the steps of:
   (a) forming a stethoscope head cover from a sheet of cloth fabric having a periphery defining an area larger than a front face of the stethoscope head, said cloth fabric being conformable to the general shape of the stethoscope head; and
   (b) removably deploying said cover over the stethoscope head such that said sheet overlies both the front face of the stethoscope head and a portion of the stethoscope head disposed behind the front face, said cover, when so deployed and when contacting the patient's body,
      (1) preventing thermal energy between the patient's body and the stethoscope head; and
      (2) transmitting sounds through the cloth fabric at a sufficient amplitude to be rendered audible by the stethoscope.

2. The method of claim 1 wherein step (b) comprises deploying said cover such that the entire front face of the stethoscope head is covered by the cloth fabric without interruption by holes or apertures.

3. The method of claim 2 wherein step (a) comprises forming said cover with an elasticized outer edge extending along the entirety of said periphery, said elasticized outer edge forming an opening smaller than a diameter of the stethoscope head so as to retain said cover on the stethoscope head.

4. The method of claim 1 further comprising the step of defining an aperture in said cloth fabric sheet, said aperture being smaller than the front face of the stethoscope head, and wherein step (b) includes deploying said cover such that said aperture is substantially centered over the front face of the stethoscope head.

5. The method of claim 4 wherein step (a) includes forming said cover with an elasticized outer edge extending along the entirety of said periphery, said elasticized outer edge forming an opening smaller than a diameter of the stethoscope head so as to retain said cover on the stethoscope head, and an elasticized inner edge surrounding said aperture.

6. The method of claim 1 wherein step (b) includes elastically engaging the stethoscope head with said cover.

7. The method of claim 1 further comprising the step of discarding said cover after a single use and replacing it on the stethoscope with a substantially identical cover.

8. The method of claim 1 wherein step (a) comprises forming said cover from flannel outing material.

9. The method of claim 1 wherein step (a) includes forming said cover as a generally circular portion of said sheet.

* * * * *